US009826690B2

(12) United States Patent
Paris

(10) Patent No.: US 9,826,690 B2
(45) Date of Patent: Nov. 28, 2017

(54) CUCURBITA PEPO HYBRIDS

(75) Inventor: Harry Stuart Paris, Yoqne'am (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 722 days.

(21) Appl. No.: 13/389,608

(22) PCT Filed: Aug. 10, 2010

(86) PCT No.: PCT/IL2010/000644
§ 371 (c)(1),
(2), (4) Date: Feb. 9, 2012

(87) PCT Pub. No.: WO2011/018785
PCT Pub. Date: Feb. 17, 2011

(65) Prior Publication Data
US 2012/0144515 A1    Jun. 7, 2012

Related U.S. Application Data

(60) Provisional application No. 61/272,029, filed on Aug. 10, 2009.

(51) Int. Cl.
*A01H 5/08*    (2006.01)
(52) U.S. Cl.
CPC ..................... *A01H 5/08* (2013.01)
(58) Field of Classification Search
CPC ....................................................... A01H 5/08
USPC ......................................................... 800/310
See application file for complete search history.

(56) References Cited

U.S. PATENT DOCUMENTS 3,879,188 A    4/1975 Fritz et al.
2007/0169216 A1    7/2007 Nicolet et al.

OTHER PUBLICATIONS

Hume et al (1983, Annals Bot. 52:689-695).*
Cohen et al (2003, Euphytica 130:433-441).*
Umiel et al (2007, Cucurbit Genet. Coop. Rep. 30:35-37).*
Zraidi et al (2007, Mol. Breeding 20:375-388).*
Paris et al (2010, HortSci. 45:1643-1644).*
Paris et al (2005, HortSci. 40:1620-1630).*
Dinner in the Yellow House, 2007, My first fried zucchini blossoms, http://www.dinnerintheyellowhouse.com/2007/06/my-first-zucchi.html.*
Communication Pursuant to Rules 70(2) and 70a(2) EPC dated Apr. 16, 2013 From the European Patent Office Re. Application No. 10808041.7.
Supplementary European Search Report and the European Search Opinion dated Mar. 28, 2013 From the European Patent Office Re. Application No. 10808041.7.
Paris et al. "Single Recessive Gene for Multiple Flowering in Summer Squash", HortScience, XP055056744, 45(11): 1643-1644, Nov. 2010.
UPOV "Explanatory Notes on the Definition of Variety Under the 1991 Act of the UPOV Convention", International Union for the Protection of New Varieties of Plants, UPOV, XP002680170, 44th Ordinary Session of the Council of UPOV, p. 1-5, Oct. 21, 2010.
International Preliminary Report on Patentability dated Feb. 23, 2012 From the International Bureau of WIPO Re. Application No. PCT/IL2010/00644.
International Search Report and the Written Opinion dated Jan. 18, 2011 From the International Searching Authority Re. Application No. PCT/IL2010/00644.
Anido et al. "Heterotic Patterns in Hybrids Involving Cultivar-Groups of Summer Squash, Cucurbita pepo L.", Euphytica, 135: 355-360, 2004. p. 355, col. 2, § 2, Abstract, p. 357, col. 1, § 1, col. 2, § 1, p. 359, col. 2, § 1, 4.
Zaidman "Israel Plant Breeder's Rights Council", Ministry of Agriculture and Rural Development, Israel Plant Breeder's Rights Gazette, Jul. 1-Dec. 31, 2009, 74: Jan. 4-18, 2010. p. 5.
Office Action dated Aug. 20, 2014 From the Israel Patent Office Re. Application No. 218065 and its Translation Into English.
Communication Pursuant to Article 94(3) EPC dated Feb. 3, 2015 From the European Patent Office Re. Application No. 10808041.7.
Communication Pursuant to Article 94(3) EPC dated Oct. 9, 2015 From the European Patent Office Re. Application No. 10808041.7.
Office Action dated Nov. 29, 2015 From the Israel Patent Office Re. Application No. 218065 and its Translation Into English.
Communication Pursuant to Article 94(3) EPC dated May 20, 2016 From the European Patent Office Re. Application No. 10808041.7.
Office Action dated Dec. 22, 2016 From the Israel Patent Office Re. Application No. 218065 and its Translation Into English. (4 Pages).

* cited by examiner

*Primary Examiner* — Anne Kubelik

(57) ABSTRACT

A plant or a part thereof, the plant being a *Cucurbita pepo* hybrid having more than one flower/fruit per node as in *Cucurbita pepo* subsp. *texana*, the fruit of the plant having the phenotype of that of *Cucurbita pepo* subsp. *pepo*.

2 Claims, 7 Drawing Sheets
(5 of 7 Drawing Sheet(s) Filed in Color)

Pumpkin

Scallop

Acorn

Crookneck

Straightneck

Vegetable Marrow

Cocozelle

Zucchini

US 9,826,690 B2

CUCURBITA PEPO HYBRIDS

RELATED APPLICATION/S

This application is a National Phase of PCT Patent Application No. PCT/IL2010/000644 having International filing date of Aug. 10, 2010, which claims the benefit of priority under 35 USC 119(e) of U.S. Provisional Patent Application No. 61/272,029 filed on Aug. 10, 2009, the contents of which are incorporated herein by reference in their entirety.

FIELD AND BACKGROUND OF THE INVENTION

The present invention, in some embodiments thereof, relates to a *Cucurbita pepo* hybrid having more than one flower/fruit per node as in *Cucurbita pepo* subsp. *texana*, the fruit of the plant having the phenotype of that of *Cucurbita pepo* subsp. *pepo*

The *Cucurbita pepo* L. is one of the most widely grown species of vegetable crops. It is the most familiar species of *Cucurbita* L., a genus native to the Americas which encompasses plants bearing edible fruits known as pumpkins and squash Like most other members of the Cucurbitaceae, *Cucurbita* plants are herbaceous, bearing large, palmate leaves and prominent fruits. Most species of *Cucurbita* are mesophytes, have fibrous root systems, and are monoecious, bearing large, intensely orange-yellow, nectar-producing, unisexual flowers that are foraged by bees. Each flower opens and is functional for one day and only during the early morning hours, withering by afternoon.

*Cucurbita pepo* is a collection of interfertile domesticated, feral, and wild plants. On the basis of allozyme variation and seed morphology, it has been classified into three subspecies, *pepo, texana*, and *fraterna*. Most cultivars belong to subsp. *pepo* but wild plants of this subspecies have not yet been found. The other cultivars belong to subsp. *texana*, which grows wild in central and southeastern U.S.A. Subsp. *fraterna* consists of wild specimens from northeastern Mexico, only.

*Cucurbita pepo* is perhaps the most polymorphic species in the plant kingdom. Its fruits range in size to over 20 kg; in shape from round to flat-scalloped, to long, bulbous cylindrical over 75 cm long; exterior color is based on hues of green, orange, and yellow, with color intensity ranging from pale to very intense, and gray contribution (darkness) ranging from none to very dark. Variegation, including striping and bicolor, can result in as many as four colors on the surface of the same fruit. Fruit mesocarp can be relatively thin or thick, and its color varies in the range from greenish white to white, yellow, light orange, and intense orange. Fruits rinds can be lignified or non-lignified, and smooth, warted, wrinkled, or netted.

*Cucurbita pepo* fruits are often used for culinary purposes when they are mature, 40 or more days past anthesis. However, the great economic value of this species rests on the common use of the young fruits, usually 2 to 5 days past anthesis, as food. These young fruits are known as summer squash. Summer squash are borne beginning approximately 50 days after seeding and as *C. pepo* grows well in a wide range of climates, it is very widespread in cultivation.

Most of the groups are centuries old. Some, the Pumpkin, the Acorn, and the Scallop, are indeed quite old, having been bred by native Americans prior to the European contact at the end of the 15th century. The Cocozelle and the Zucchini originated in southern and northern Italy, respectively. The Cocozelle is an old group, with records dating to the late 16th century, and the Zucchini is the youngest group, with records dating only to the beginning of the 20th century. The Cocozelle has some economic importance in Europe and in Israel yet, today, the Zucchini is by far the economically most important cultivar-group of *Cucurbita pepo*, perhaps exceeding in economic value the rest of the species, indeed, the rest of the genus combined.

Due to the high commercial value resting in the flowers and young fruits of *Cucurbita pepo* there is a need to develop new cultivars of this species having higher yields.

SUMMARY OF THE INVENTION

According to an aspect of some embodiments of the present invention there is provided a plant or a part thereof, the plant being a *Cucurbita pepo* hybrid having more than one flower/fruit per node as in *Cucurbita pepo* subsp. *texana*, the fruit of the plant having the phenotype of that of *Cucurbita pepo* subsp. *pepo*.

According to an aspect of some embodiments of the present invention there is provided a plant or a part thereof, the plant being a hybrid *Cucurbita pepo* subsp. *pepo*, having more than one flower/fruit per node at most nodes, the fruit of the plant having the phenotype of that of *Cucurbita pepo* subsp. *pepo*.

According to an aspect of some embodiments of the present invention there is provided a plant or a part thereof of *Cucurbita pepo* selected from a population of progeny of the hybrid produced by crossing *Cucurbita pepo* subsp. *texana* and *Cucurbita pepo* subsp. *pepo*, the plant having more than one flower/fruit per node as in *Cucurbita pepo* subsp. *texana*, the fruit of the plant having the phenotype of that of *Cucurbita pepo* subsp. *pepo*.

According to an aspect of some embodiments of the present invention there is provided a plant or a part thereof, the plant being a *Cucurbita pepo* Zucchini hybrid, whose seeds have been deposited as Accession No. NCIMB 41744 (herein referred to as Multizuq).

According to an aspect of some embodiments of the present invention there is provided a plant or a part thereof, the plant being a *Cucurbita pepo* Cocozelle hybrid, whose seeds have been deposited as Accession No. NCIMB41794 (herein referred to as Nizzan).

According to an aspect of some embodiments of the present invention there is provided a cell having the genome of the plant.

According to an aspect of some embodiments of the present invention there is provided a culture comprising a plurality of the cells.

According to some embodiments of the invention, the plant part is selected from the group consisting of roots, stems, leaves, cotyledons, flowers, fruit, embryos, pollen, and seeds.

According to some embodiments of the invention, the cell being regeneratable.

According to an aspect of some embodiments of the present invention there is provided a method of producing a *Cucurbita pepo* hybrid, the method comprising:
(a) crossing *Cucurbita pepo* subsp. *texana* with *Cucurbita pepo* subsp. *pepo*;
(b) selecting progeny individuals from said crossing having more than one flower/fruit per node as in *Cucurbita pepo* subsp. *texana*, the fruit of said individuals having the phenotype of that of *Cucurbita pepo* subsp. *pepo*.

According to some embodiments of the invention, the method further comprising:

(c) backcrossing individuals selected in step (b) with *Cucurbita pepo* subsp. *pepo*.

According to some embodiments of the invention, said method additionally comprises the step of propagating said individuals following step (b) or (c).

According to some embodiments of the invention, the step of propagating includes the step of vegetative propagation.

According to some embodiments of the invention, the step of propagating includes the step of propagation by seed.

According to an aspect of some embodiments of the present invention there is provided a method for producing a *Cucurbita pepo* hybrid seed comprising crossing a first parent *Cucurbita pepo* plant with a second parent *Cucurbita pepo* plant and harvesting the resultant hybrid $F_1$ seed, wherein at least one of the first or the second parent *Cucurbita pep*. plant is the above plant.

According to an aspect of some embodiments of the present invention there is provided a hybrid seed produced by the above-method.

According to an aspect of some embodiments of the present invention there is provided a hybrid plant, or parts thereof, produced by growing the hybrid seed.

According to an aspect of some embodiments of the present invention there is provided a method of generating a *Cucurbita pepo* fruits and/or flowers, the method comprising:

(a) seeding seeds the above-hybrid and/or planting seedlings of said seeds;
(b) growing plants generated from said seeds or said seedlings; and
(c) harvesting the fruits and/or flowers of said plants, thereby generating the *Cucurbita pepo* fruits and/or flowers.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings.

DESCRIPTION OF SPECIFIC EMBODIMENTS OF THE INVENTION

Figure 1:
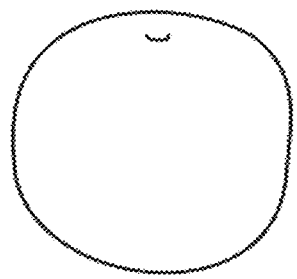
FIG. 1 is a schematic representation of fruit shape of the eight edible cultivar-groups of *Cucurbita pepo* (after Paris, 1986, prior art figure).
Figure 1:
Figure 1:
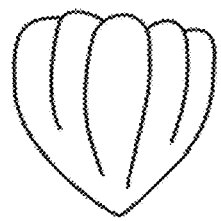
Figure 1:
Figure 1:
Figure 1:
Figure 1:
Figure 1:

The present invention, in some embodiments thereof, relates to a *Cucurbita pepo* hybrid having more than one flower/fruit per node as in *Cucurbita pepo* subsp. *texana*, the fruit of the plant having the phenotype of that of *Cucurbita pepo* subsp. *pepo*.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Vegetables of the *Cucurbita pepo* species are of significant economic importance as they encompass many coveted summer and winter edible types as well as ornamental gourds. *Cucurbita pepo* refers to what are commonly known as the summer squash, that is, cocozelle, vegetable marrow, scallop, zucchini, straightneck and crookneck types and winter squash such as acorn and pumpkin.

Accordingly, the inventor of the present invention has evaluated options for increasing fruit/flower yield of *Cucurbita pepo*.

The inventor noticed that there is a difference in the number of flowers borne in and next to the leaf axils in *Cucurbita pepo*: in *C. pepo* subsp. *pepo*, only one flower bud is formed in or next to each leaf axil. However, in *C. pepo* subsp. *texana*, more than one flower can be borne in or next to the leaf axil in each of its four edible-fruited cultivar-groups. This characteristic is most strongly expressed in the Crookneck Group, in which three or even more flowers can be found in or next to the leaf axils. When two or more female flowers are produced, plants of Crookneck cultivars can produce more than one fruit at the same node. Some Crookneck cultivars, such as 'Supersett', are known to be extremely high yielding.

The present invention is of *Cucurbita pepo* hybrids having more than one flower/fruit per node (as in *Cucurbita pepo* subsp. *texana*), but with the appearance of the fruit of *Cucurbita pepo* subsp. *pepo*.

This invention was demonstrated by the development Zucchini and Cocozelle hybrids having the multiple-flowering characteristic. This was accomplished by plant breeding methodology, specifically, the backcross-pedigree selection method (Allard, 1960). As the donor of the multiple-flowering characteristic, the Crookneck, is so distant in genealogy from the Zucchini and the Cocozelle, this became a long and tedious process, but unexpectedly and surprisingly appears to have been successful.

Thus, according to an aspect of the invention there is provided a plant or a part thereof, the plant being a *Cucurbita pepo* hybrid having more than one flower/fruit per node as in *Cucurbita pepo* subsp. *texana*, the fruit of the plant having the phenotype of that of *Cucurbita pepo* subsp. *pepo*.

According to an aspect of the invention there is provided a plant or a part thereof, the plant being a hybrid *Cucurbita pepo* subsp. *pepo*, having more than one flower/fruit per node at most nodes (i.e., more than 50% of the nodes), the fruit of the plant having the phenotype of that of *Cucurbita pepo* subsp. *pepo*.

According to an aspect of the invention there is provided a plant or a part thereof of *Cucurbita pepo* selected from a population of progeny of the hybrid produced by crossing *Cucurbita pepo* subsp. *texana* and *Cucurbita pepo* subsp. *pepo*, the plant having more than one flower/fruit per node as in *Cucurbita pepo* subsp. *texana*, the fruit of the plant having the phenotype of that of *Cucurbita pepo* subsp. *pepo*.

The phrase "plant or part thereof" as used herein encompasses whole plants, ancestors and progeny of the plants and plant parts, including seeds, fruits, flowers, shoots, stems, roots (including tubers), pollen, embryo, cotyledons, leaves and plant cells, tissues and organs. The plant may be in any form including suspension cultures, embryos, meristematic regions, callus tissue, leaves, gametophytes, sporophytes, pollen, ovules and microspores.

As used herein "*Cucurbita pepo*" refers to the collection of interfertile domesticated, feral and wild plants of the subspecies *pepo, texana,* and *fraterna*.

As used herein the term "hybrid" refers to the offspring derived from crossing two parental breeding lines of *Cucurbita pepo*.

The hybrid is heterozygous and derived from the crossing of the two parental breeding lines, each of which is nearly homozygous. The hybrid and each of its two parent breeding lines are homogeneous populations. The hybrid and its parents according to the invention contain, however, at least a small portion of the genome, by introgression, of *Cucurbita pepo* subsp. *texana*, specifically, the gene or genes conferring the production of more than one flower/fruit per node and adjacent chromosomal regions.

Figure 2:
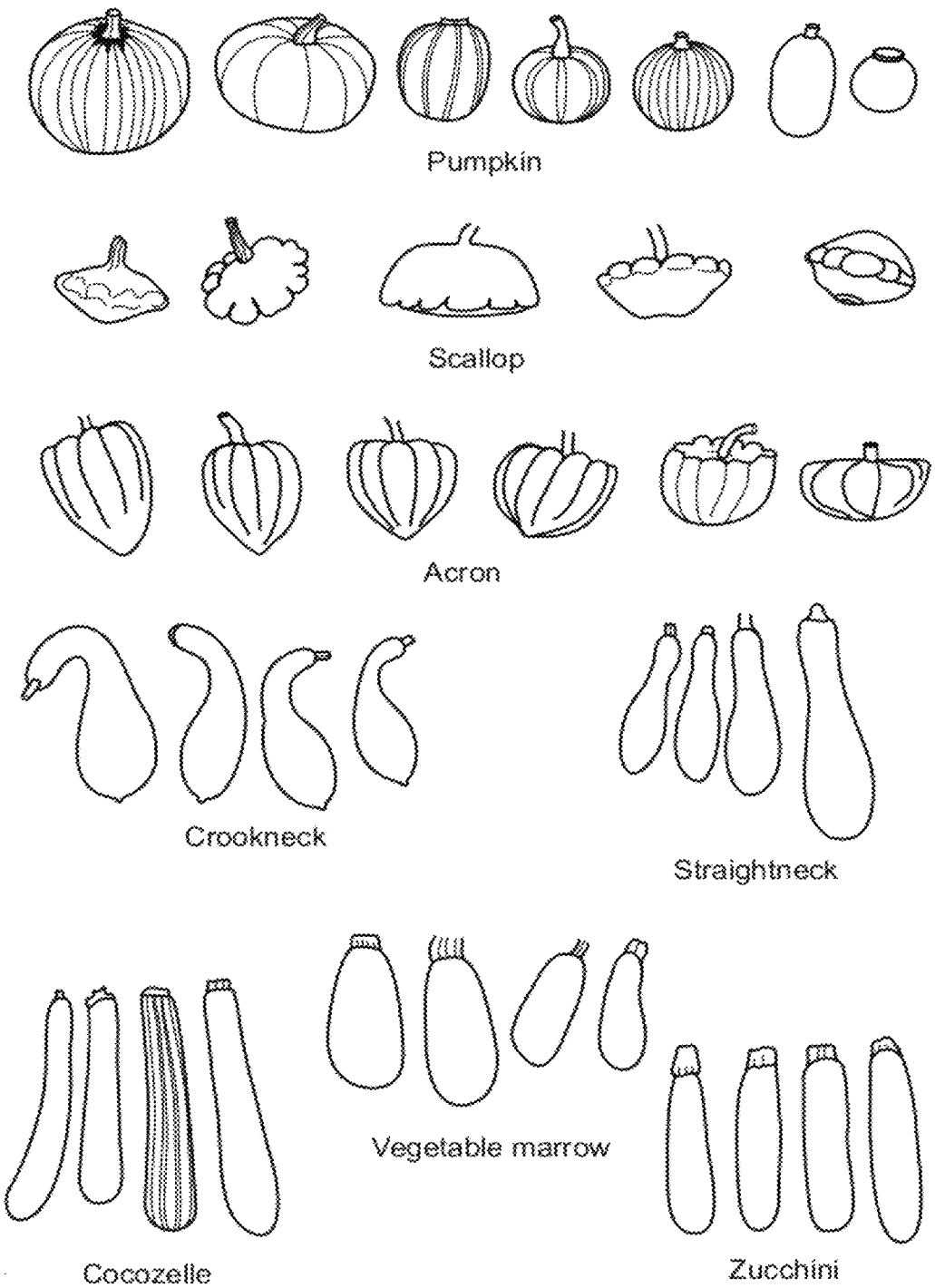
FIG. 2 is an expanded schematic representation of fruit shape of the eight edible-cultivar-groups of *Cucurbita pepo*.
Figure 3:
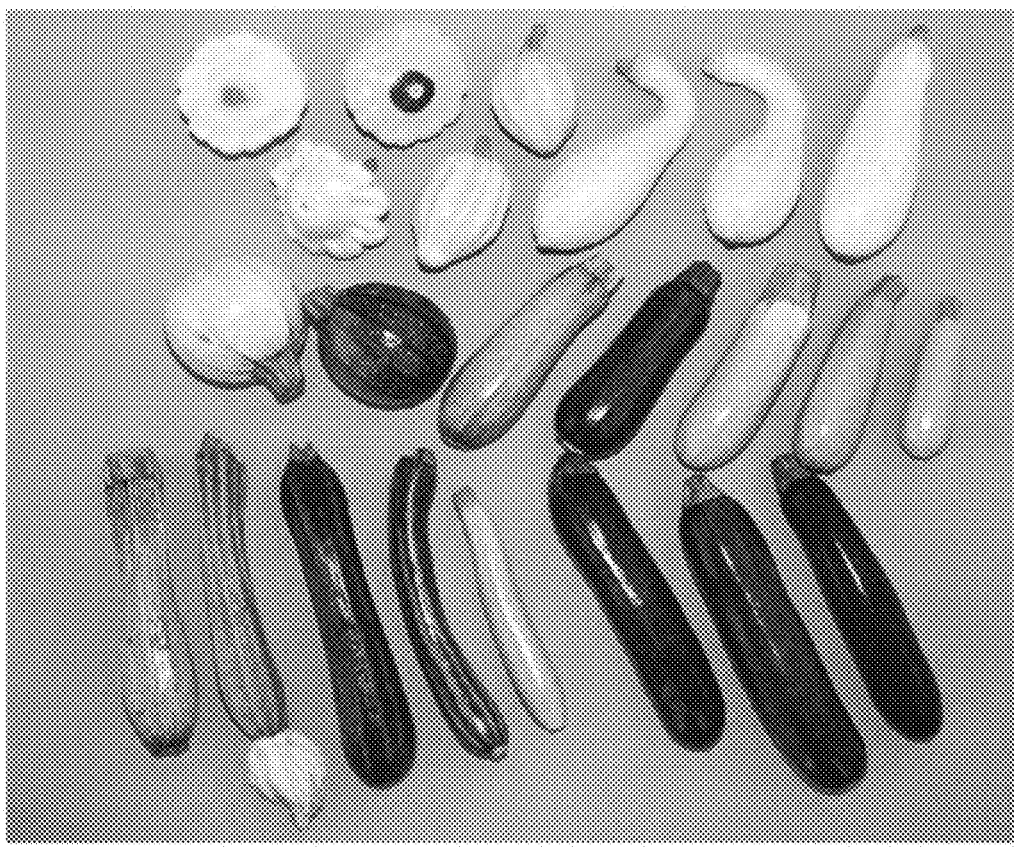
FIG. 3 is a photograph showing representative immature (2-5 days past anthesis) fruits of 23 cultivars *Cucurbita pepo*, at least one from each of the edible-fruited cultivar groups. Left to right, top row, Scallop Group: 'Yellow Bush Scallop', 'Belye', and "Sunburst"; Acorn group: 'Royal Acorn' and 'Table Queen'; Crookneck Group: 'Early Golden Crookneck' and 'Yellow Summer Crookneck'; Straightneck Group: 'Early Prolific Straightneck'; center row, Pumpkin Group: 'Ronde de Nice' and 'Tondo Scuro di Piancenza'; Vegetable Marrow Group: 'Verte Petite d'Alger' (syn. 'Grey Zucchini'), 'All Green Bush', 'Beirut', 'Long Green', and 'Sihi Lavan'; bottom row, Cocozelle Group: 'Romanesco', 'Lung di Toscana' (with corolla and calyx), 'Long Cocozelle', 'Striato d'Italia', and 'Lung Bianco di Sicilia'; Zucchini Group: 'Black Zucchini', 'Nano Verde di Milano', and 'True French'.

On the basis of fruit shape, *Cucurbita pepo* is considered to consist of eight edible-fruited cultivar-groups (FIGS. 1, 2, and 3), four of which are classified in *C. pepo* subsp. *pepo* and the other four in *C. pepo* subsp. *texana*. Description of the eight groups and their placement in the two cultivated subspecies are summarized in Table 1, below. The fruits of two of the cultivar-groups, Pumpkin and Acorn, are used primarily when mature. Pumpkin fruits are round, being spherical, oblate, globular, or oval and Acorn fruits are turbinate with alternating longitudinal ridges and furrows. In both of these groups, the length-to-width ratio of the fruits is approximately 1:1. The fruits of the other six cultivar-groups are used when immature, as summer squash, and diverge markedly from this 1:1 ratio. Scallop squash are flat and scalloped, hence having a length-to-width ratio that is considerably less than 1:1. The other five groups, Cocozelle, Crookneck, Straightneck, Vegetable Marrow, and Zucchini, have a length-to-width ratio that is considerably greater than 1:1 (Table 1, below). Each cultivar-group of both subspecies is comprised of numerous cultivars. The name of one representative cultivar of each cultivar-group is given in Table 1.

Plants of the invention have more than one flower/fruit per node. Flower buds in *Cucurbita pepo* are differentiated in or beside the leaf axils, that is, at the junctions of the petiole bases with the stem; these junctions are also referred to as stem nodes. Thus, according to embodiments of the invention, 2, 3, 4 or even more flower buds can be formed at each stem node.

As mentioned, plants of the invention produce more than one flower at most stem nodes and have fruits which are endowed with the phenotype of *Cucurbita pepo* subsp. *pepo*. The potentially higher yield of flowers and fruits per hybrid plant as compared to all previously existing *Cucurbita pepo* subsp. *pepo* does not compromise fruit phenotype.

As used herein "fruit phenotype" refers to the fruit shape, specifically, fruit profile and topography. Table 1 below lists the fruit shape profiles of the cultivar-groups belonging to *Cucurbita pepo* subsp. *pepo* and *C. pepo* subsp. *texana*. The fruits of *C. pepo* subsp. *pepo* can be differentiated from those of *C. pepo* subsp. *texana* in fruit topography. The fruits of the Cocozelle Group are nearly smooth to obviously ribbed along their longitudinal axis. The Zucchini has uniformly cylindrical fruits which are slightly ribbed along their longitudinal axis. These ribs are promontories occurring above the 10 main vascular tracts running along the longitudinal axis of the fruits. In contrast, the fruits of the cultivar-groups of *C. pepo* subsp. *texana*, have furrows along their longitudinal axis. These furrows are depressions occurring above the 10 main vascular tracts. Both, ribs and furrows, are easily observed in cross-cut sections of the fruits.

TABLE I

The edible-fruited cultivar-groups of *Cucurbita pepo* (after Paris, 2000).

| Cultivar-group | Synonyms | Subspecies | Standard cultivar | Fruit shape |
|---|---|---|---|---|
| Pumpkin | | *pepo* | Connecticut Field | Round: spherical oblate, ovate, globular |
| Vegetable Marrow | Middle eastern | *pepo* | Beirut | Short, tapered cylindrical, narrow at peduncle end, broad at stylar end, length-to-broadest width ratio ranging from 1.5-3.0 |
| Cocozelle | Italian | *pepo* | Striato d'Italia | Long to extremely long, cylindrical, bulbous near stylar end, length-to-broadest width ratio at least 3.5 |
| Zucchini | Courgette | *pepo* | Black Zucchini | Uniformly cylindrical, length-to-broadest width ratio 3.5-5.0 |
| Acorn | Table Queen | *texana* | Table Queen | Turbinate, furrowed, broad at peduncle end, convex at stylar end |
| Crookneck | | *texana* | Yellow Summer Crookneck | Elongated, with narrow, slightly to very curved neck, broad stylar half, convex stylar end |

TABLE I-continued

The edible-fruited cultivar-groups of *Cucurbita pepo* (after Paris, 2000).

| Cultivar-group | Synonyms | Subspecies | Standard cultivar | Fruit shape |
|---|---|---|---|---|
| Scallop | Patty Pan, Patisson | *texana* | Golden Bush Scallop | Flattened, with scalloped margins |
| Straightneck | | *texana* | Early Prolific Straightneck | Cylindrical, with short neck or constriction near the stem end and broad stylar half, convex or pointed distal end |

According to one embodiment of the invention the hybrid plant is a Zucchini and crookneck hybrid.

One specific embodiment of the invention is the hybrid 'Multizuq', which is the F1 hybrid of zucchini breeding line 1688-1-3-16 crossed with zucchini breeding line 1477-1-7-2-10. Seeds of 'Multizuq' were deposited under the Budapest treaty on Jul. 30, 2010 at the NCIMB Ltd. Scotland UK, under the accession number NCIMB 41744.

According to one embodiment of the invention the hybrid plant is a cocozelle and crookneck hybrid.

One other specific embodiment of the invention is the hybrid 'Nizzan', which is the F1 hybrid of cocozelle breeding line 1260-4-6-2-10 crossed with cocozelle breeding line 1413-4-54-7. Seeds of Nizzan were deposited under the Budapest treaty on Dec. 10, 2010 at the NCIMB Ltd. Scotland UK. under the accession number 41794.

The invention also relates to a cell having the genome of the plant of the invention i.e., having more than one flower/fruit per node as in *Cucurbita pepo* subsp. *texana*, the fruit of the plant having the phenotype of that of *Cucurbita pepo* subsp. *pepo*. According to a specific embodiment the cells are regenerable.

The invention also relates to a culture comprising a plurality of the cells.

According to an embodiment of the invention the plant is selected from a population of progeny of the hybrid produced by crossing within *Cucurbita pepo* subsp. *pepo*, the plant having more than one flower/fruit per node as in *Cucurbita pepo* subsp. *texana*, the fruit of the plant having the phenotype of that of *Cucurbita pepo* subsp. *pepo*.

Thus according to an aspect of the invention there is provided a method of producing a *Cucurbita pepo* hybrid, the method comprising:
(a) crossing *Cucurbita pepo* subsp. *texana* with *Cucurbita pepo* subsp. *pepo*;
(b) selecting a progeny individuals from said crossing having more than one flower/fruit per node as in *Cucurbita pepo* subsp. *texana*, the fruit of said individuals having the phenotype of that of *Cucurbita pepo* subsp. *pepo*.

According to a specific embodiment, the method further comprising:
(c) backcrossing individuals selected in step (b) with *Cucurbita pepo* subsp. *pepo*.

The term "backcrossing" as used herein refers to the repeated crossing back to elite breeding lines of *C. pepo* subsp. *pepo*. The parental plant which contributes the desired characteristic is termed the donor parent. This terminology refers to the fact that the donor parent is used once, in the initial cross. The parental line to which the special characteristice from the donor parent is introgressed is known as the recurrent parent, as it is used repeatedly (recurrently) in the backcrossing protocol.

In a typical backcross protocol, a plant from the original line of interest (recurrent parent) is crossed with a plant from the second variety, the donor parent, which carries the single special characteristic of interest. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred (introgressed) characteristic from the donor parent.

Backcrossing methods can be used with the present invention to improve or introduce a unique characteristic into the parent lines.

According to a specific embodiment the method additionally comprises the step of propagating said individuals following step (b) or (c).

According to a specific embodiment the method the step of propagating includes the step of vegetative propagation.

According to a specific embodiment the method the step of propagating includes the step of propagation by seed.

The development of hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5; etc.

A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield

*Cucurbita pepo* plants can be easily cross-pollinated. A trait is readily transferred from one plant to another plant, including *Cucurbita pepo* plants of different subspecies, using conventional breeding techniques, for example to obtain new commercializable hybrids. The introgression of a trait into the elite line is for example achieved by recurrent selection breeding, for example by backcrossing. In this case, the elite line (recurrent parent) is first crossed to a donor inbred (the non-recurrent parent) that carries the trait. The progeny of this cross is then mated back to the recurrent parent followed by selection in the resultant progeny for the trait. After three, preferably four, more preferably five or more generations of backcrosses with the recurrent parent with selection for the trait, the progeny is heterozygous for the locus harboring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1:Theory and Technique, 360-376, incorporated herein by reference). Selection for the trait is carried out after each cross.

In one embodiment, a plant of the present invention is an inbred, a hybrid, or a dihaploid, for example produced by pedigree breeding or by recurrent selection breeding. In one embodiment, a plant of the present invention has commercially acceptable horticultural characteristics.

In one embodiment, the present invention discloses a method of producing seed of a plant of the present invention (i.e., having more than one flower/fruit per node as in *Cucurbita pepo* subsp. *texana*, the fruit of the plant having the phenotype of that of *Cucurbita pepo* subsp. *pepo*) comprising: a) growing a plant of the invention; b) allowing said plant to self-pollinate; c) harvesting seeds from said plant.

As mentioned plants can also be propagated vegetatively
  using methods well-known in the art, for example in-vitro plant tissue culture, rooting side shoot or protoplast fusion. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets; d) growing plants from said rooted plantlets; and harvesting seeds from said plants.

Plants of the invention (i.e., having more than one flower/fruit per node as in *Cucurbita pepo* subsp. *texana*, the fruit of the plant having the phenotype of that of *Cucurbita pepo* subsp. *pepo*) can also be transformed genetically with a gene of interest, using techniques well known in the art. Accordingly, the present invention also further discloses a *Cucurbita pepo* plant according to the instant invention, such as a gene of interest.

In one embodiment, the present application discloses methods of producing a fruit/flower, comprising growing a plant of the invention until a fruit or flower is produced and harvesting the fruit or flower. It will be appreciated that although the instant specification places an emphasis on fruit yield in *Cucurbita pepo*, the flowers have a culinary as well as ornamental value and therefore the present teachings are meant to encompass both fruit and flower products.

As used herein the term "about" refers to ±10%.

The terms "comprises", "comprising", "includes", "including", "having" and their conjugates mean "including but not limited to".

The term "consisting" of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998);

methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIAL AND METHODS

Multiple flowering in Zucchini was realized in the development of the $F_1$ hybrid 'Multizuq' and its parents. These developments were the outcome of a complex series of crossing. The initial cross, designated No. 755, was made at the A.R.O. Newe Ya'ar Research Center, northern Israel. The female parent, the parent having the multiple-flowering characteristic, was the Crookneck hybrid 'Supersett' and the male parent was the open-pollinated Cocozelle 'Striato Pugliese'. Seeds of 'Supersett' had been from Joseph Harris Co., Rochester, N.Y. and seeds of 'Striato Pugliese' had been obtained from Emanuele Larosa, Bari, Italy. $F_1$ plants were self-pollinated and an $F_2$ plant having the multiple-flowering characteristic of 'Supersett' was then crossed with an inbred of the open-pollinated Zucchini 'True French'. Seeds of 'True French' had been obtained from Thompson & Morgan, U.K. $F_1$ plants were self-pollinated and some $F_2$ plants having multiple flowering were obtained. From this point on, a divergence into two separate parental lines was undertaken.

In the female parent line of 'Multizuq', a cross was made with a Zucchini inbred developed at Newe Ya'ar, herein designated 1-16. The $F_1$ was selfed, again $F_2$s were grown out and selected for multiple flowering, and this time were crossed on a different Zucchini inbred developed at Newe Ya'ar, herein designated 16-33. This was followed by four more cycles of backcrossing and selfing to the same, 16-33, inbred, following by three of generations of selfing to give the female parent of 'Multizuq', designated 1688-1-3-16.

In the male parent line of 'Multizuq', a multiple-flowering $F_2$ plant was backcrossed on 'True French'. A new $F_2$ was obtained and a multiple-flowering individual was crossed on inbred 1-16. Once again, a self-pollination was made and a multiple-flowering $F_2$ plant was crossed again with inbred 1-16. After self-pollination, a multiple-flowering $F_2$ plant was crossed with a double-cross hybrid of complex parentage. Finally, this was crossed again with 1-16, and an individual in the $F_2$ selected for multiple flowering. This was followed by four more generations of selfing to give the male parent of 'Multizuq', designated 1477-1-7-2-10.

'Multizuq', therefore, is the $F_1$ hybrid of 1688-1-3-16 crossed with 1477-1-7-2-10.

Multiple flowering in Cocozelle was realized in the development of the $F_1$ hybrid 'Nizzan' and its parents. These developments were the outcome of a complex series of crossing. The initial crosses were the same as in the development of 'Multizuq', through the stage of selecting a multiple-flowering individual in the $F_2$ of the cross with inbred 1-16. In the female parent line of 'Nizzan', this $F_2$ multiple flowering individual was crossed with a Cocozelle inbred developed at Newe Ya'ar, herein designated 1-8-13. This was followed by four of generations of selfing to give the female parent of 'Nizzan', designated 1260-4-6-2-10.

In the male parent line of 'Nizzan', a multiple-flowering plant of the same $F_2$ was crossed on an inbred, designated 1-7, that was derived from a complex cross consisting mostly of Cocozelle parentage. A self-pollination was made on this $F_1$ and a multiple-flowering plant in the resulting $F_2$ was crossed with a commercially available Cocozelle $F_1$ hybrid. After self-pollination of a plant of this cross, a multiple-flowering $F_2$ plant was selected and self-pollinated. Self-pollination was repeated for several more generations until the true-breeding, multiple-flowering Cocozelle inbred designated 1413-4-54-7 was derived, which serves as the male parent of 'Nizzan'.

'Nizzan', therefore, is the $F_1$ hybrid of 1260-4-6-2-10 crossed with 1413-4-54-7.

RESULTS

Figure 4:
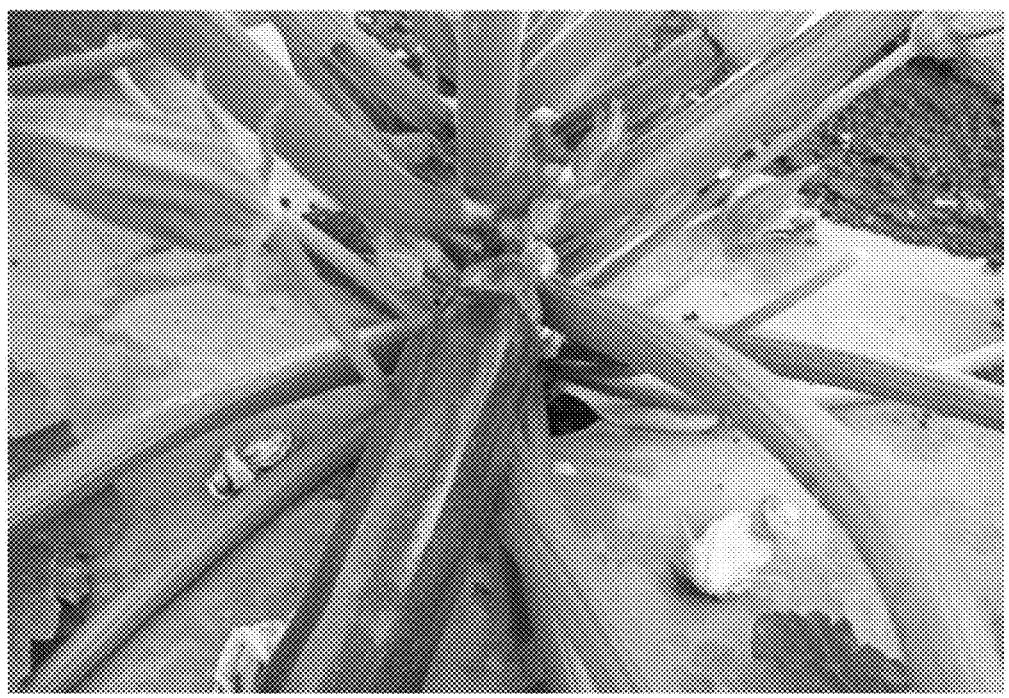
FIG. 4 is a photograph of a plant of 'Multizuq' Zucchini hybrid. Note the Zucchini-type fruit and the presence of more that one flower bud per leaf axil.
Figure 5:
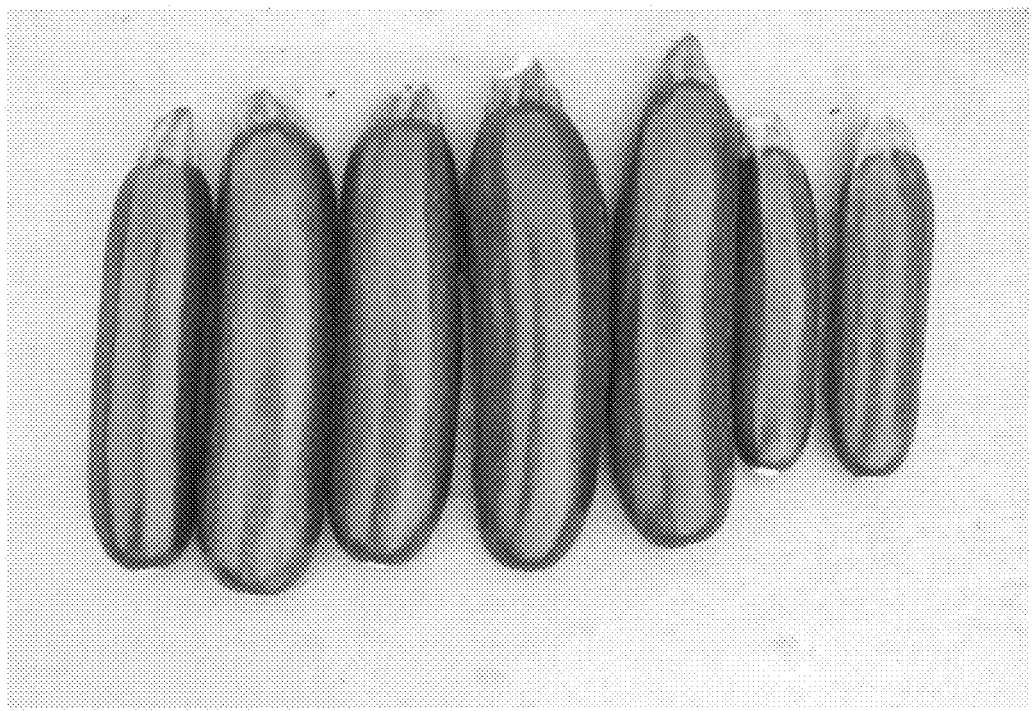
FIG. 5 is photograph showing fruits of 'Multizuq' Zucchini squash hybrid.

'Multizuq' is a multiple-flowering hybrid Zucchini. It has open, non-branching, relatively small plants. The petioles are fairly smooth and the laminae are silver-mottled. More than one flower bud is formed in or beside the leaf axils, that is, at the junctions of the petiole bases with the stem (FIG. 4). The flower buds are usually not of the same size and do not reach anthesis on the same day. One or more of these buds may be male and one or more may be female. The fruits are typically Zucchini by being uniformly cylindrical of length-to-width ratio approximating 4:1 (Table 1). When young, at the summer squash age (2-5 days past anthesis), they are glossy and very intensely green (FIG. 5). The stylar scar is fairly small and the peduncle, while relatively short and thick, detaches easily from the stem when the fruit is picked. This hybrid is expected to realize its greatest potential in yield when grown under long-season, greenhouse conditions.

Figure 6:
FIG. 6 is a photograph showing a plant of 'Nizzan' Cocozelle hybrid. Note the presence of more than one flower bud per leaf axil.
Figure 7:
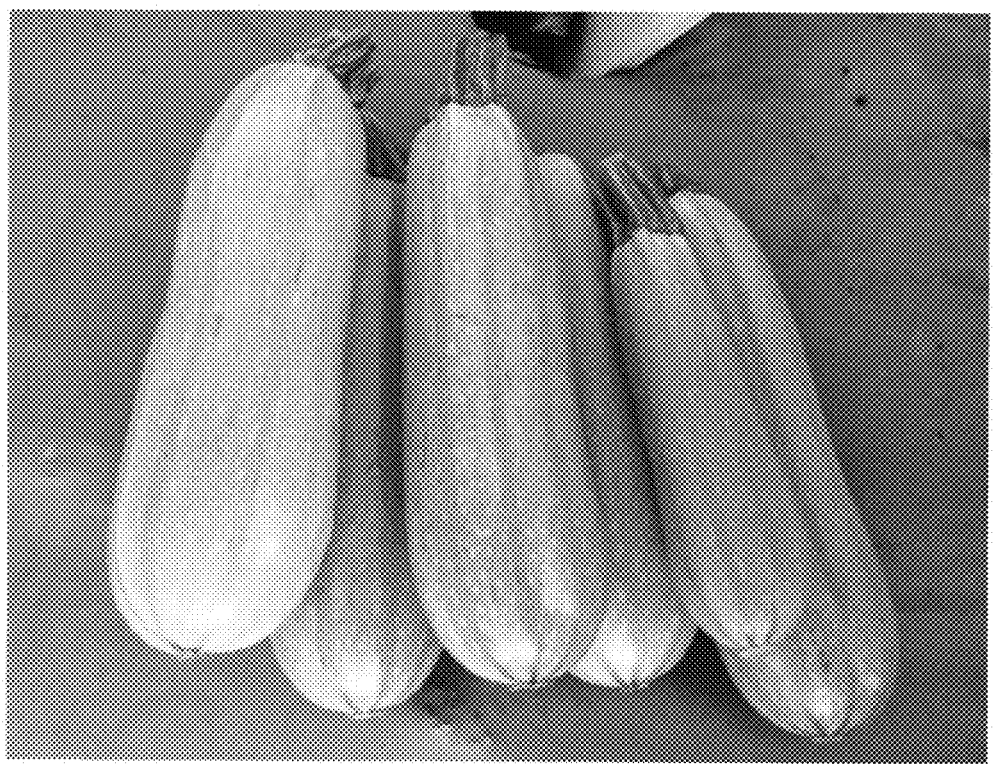
FIG. 7 is a photograph showing fruits of 'Nizzan' Cocozelle squash hybrid.

'Nizzan' is a multiple-flowering hybrid Cocozelle. It has open, non-branching, relatively small plants. The petioles are fairly smooth and the laminae are silver-mottled. More than one flower bud is formed in or beside the leaf axils, that is, at the junctions of the petiole bases with the stem (FIG. 6). The flower buds are usually not of the same size and do not reach anthesis on the same day. One or more of these buds may be male and one or more may be female. The fruits are typically Cocozelle by being long and bulbously cylindrical, of length-to-broadest-width ratio approximating 4:1 (Table 1). When young, at the summer squash age (2-5 days past anthesis), they are glossy and light green (FIG. 7). The stylar scar is fairly small and the peduncle is relatively long and narrow, detaching easily from the stem when the fruit is picked. This hybrid is expected to realize its greatest potential in yield when grown under long-season, greenhouse conditions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

LITERATURE CITED

Other References are Listed Throughout the Specification

Allard, R. W. 1960. Principles of plant breeding, pp. 43-49. Wiley, N.Y.

Decker, D. S. 1985. Numerical analyzsis of allozyme variation in *Cucurbita pepo*. Econ. Bot. 39:300-309.

Decker, D. S. 1988. Origin(s), evoluation, and systematics of *Cucurbita pepo*. Econ. Bot. 42: 4-15.

Duchesne, A. N. 1786. Essai sur l'histoire naturelle des courges. Panckoucke, Paris.

Ferriol, M., B. Pico, and F. Nuez. 2003. Genetic diversity of a germplasm collection of *Cucurbita pepo* using SRAP and AFLP markers. Theor. Appl. Genet. 107: 271-282.

Paris, H. S. 1986. A proposed subspecific classification for *Cucurbita pepo*. Phytologia 61: 133-138.

Paris, H. S. 1989. Historical records, origins, and development of the edible cultivar groups of *Cucurbita pepo* (Cucurbitaceae). Econ. Bot. 43: 423-443.

Paris, H. S. 2000. History of the cultivar-groups of *Cucurbita pepo*, pp. 71-170, 4 pl., in J. Janick, editor, Horticultural Reviews 25(2001). Wiley, N.Y.

Paris, H. S. 2007. The drawings of Antoine Nicolas Duchesne for his natural history of the gourds. Museum National d'Histoire Naturelle, Paris.

Paris, H. S. 2008. Summer squash, pp. 351-379, in: J. Prohens and F. Nuez, editors, Handbook of Plant Breeding, Vegetables I. Springer, N.Y.

Paris, H. S., N. Yonash, V. Portnoy, N. Mozes-Daube, G. Tzuri, and N. Katzir. 2003. Assessment of genetic relationships in *Cucurbita pepo* (Cucurbitaceae) using AFLP, ISSR, and SSR markers. Theor. Appl. Genet. 106: 971-978.

What is claimed is:

1. A plant, the plant being a *Cucurbita pepo* Zucchini hybrid obtained from seeds which have been deposited as Accession No. NCIMB 41744.

2. A plant, the plant being a *Cucurbita pepo* Cocozelle hybrid obtained from seeds which have been deposited as Accession No. NCIMB 41794.

* * * * *